United States Patent [19]

Nashef et al.

[11] Patent Number: 4,678,470
[45] Date of Patent: Jul. 7, 1987

[54] BONE-GRAFTING MATERIAL

[75] Inventors: Aws S. Nashef, Costa Mesa; Todd D. Campbell, Corona, both of Calif.

[73] Assignee: American Hospital Supply Corporation, Evanston, Ill.

[21] Appl. No.: 738,993

[22] Filed: May 29, 1985

[51] Int. Cl.$^4$ .............................................. A61F 2/00
[52] U.S. Cl. ..................................................... 623/16
[58] Field of Search ................................... 623/16, 66

[56] References Cited

U.S. PATENT DOCUMENTS

| | | |
|---|---|---|
| 4,120,730 | 10/1978 | Trojer et al. . |
| 4,257,405 | 3/1981 | Colville . |
| 4,277,238 | 7/1981 | Kategiri . |
| 4,309,488 | 1/1982 | Heide et al. . |
| 4,330,891 | 5/1982 | Branemark et al. . |
| 4,349,470 | 9/1982 | Battista ................................... 623/16 |
| 4,394,370 | 7/1983 | Jefferies . |
| 4,407,793 | 10/1983 | Akimova et al. . |
| 4,440,750 | 4/1984 | Glowacki . |
| 4,472,840 | 9/1984 | Jefferies . |
| 4,485,096 | 11/1984 | Bell . |
| 4,485,097 | 11/1984 | Bell . |

OTHER PUBLICATIONS

Narang et al., *J. Oral Maxillofac. Surg. (U.S.)*, vol. 40, No. 3, pp. 133–141, Mar. 1982.

Glowacki et al., *Calcified Tissue International*, vol. 33, pp. 71–76, 1981.

Wittbjer et al., *Scand. J. Plast. Reconstr. Surg.*, vol. 16, pp. 239–244, 1982.

Takagi et al., *Ann. Surg.*, vol. 196, No. 1, pp. 100–109, Jul. 1982.

Gupta et al., *International Orthopaedics*, vol. 6, pp. 79–85, 1982.

Gupta and Tuli, *Acta Orthop. Scand.*, vol. 53, pp. 857–865, 1982.

Gross et al. *Oral. Surg.*, vol. 49, No. 1, pp. 21–26, Jan. 1980.

Urist et al., *Proc. Nat'l. Acad. Sci. U.S.A.*, vol. 76, No. 4, pp. 1828–1832, Apr. 1979.

*Primary Examiner*—Gregory E. McNeill
*Attorney, Agent, or Firm*—Bernard, Rothwell & Brown

[57] ABSTRACT

A bone grafting material is derived from allogenic or xenogenic bone by a process that includes tanning with glutaraldehyde. The bone may be pulverized, used as a large block, or machined into a precise pre-determined shape, depending on the bone defect to be repaired. Glutaraldehyde tanning of bone yields a stabilized, highly biocompatible, and non-antigenic material which becomes incorporated into host bone when placed adjacent to it.

27 Claims, No Drawings

BONE-GRAFTING MATERIAL

BACKGROUND OF THE INVENTION

Bridging of large bone defects such as those which occur as a result of traumatic extrusion, radial tumor resection and massive sequestration due to infection is one of the most challenging orthopedic problems. Fresh autogenous bone is regarded as the best grafting material. However, there are cases in which sufficient quantities of autogenous bone are not available or the secondary surgery to obtain bone is too severe and traumatic.

The use of exogenous material may decrease the need for secondary surgery to obtain suitable graft material. Furthermore, failure of bone autografts is between 13-30% and is even higher when allogenic frozen or freeze-dried bone is used. Clearly then, there is a need for a suitable graft material that can be used in repair of bone defects including those secondary to tumor, trauma, and osteomyelitis.

Several attempts to use exogeneous bone graft material have been tried with varying degrees of success. Basically two approaches have been taken: osteoinduction and osteoinvasion. The main difference between these methods is the mode of host bone ingrowth. Osteoinductive bone grafts rely on the bone graft to induce osteogenic precursor cells in marrow and connective tissues surrounding the graft to dedifferentiate and give rise to new bone formations. Osteoinvasive bone grafts rely on host cells migrating into the graft and producing new bone formations.

Of the two processes, the osteoinductive grafts have been more successful than the osteoinvasive grafts. Typically the osteoinductive grafts have been incorporated into the host bone within a 2-6 week period, whereas osteoinvasive grafts have been found to be non-incorporated as long as 1 year from implantation.

SUMMARY OF THE INVENTION

Disclosed is a method of deriving a biocompatible, non-antigenic, and incorporatable bone grafting material from allogenic or xenogenic bone. The bone may be pulverized, used as a large block, or machined into a precise pre-determined shape, depending on the bone defect to be repaired. The method of deriving the material comprises tanning the bone with glutaraldehyde. This tanning procedure has been found to yield a stabilized, non-antigenic, and highly biocompatible material which is osteoinvasive. Host bone adjacent to the grafting material has been found to have invaded it in as little as 3 months.

DETAILED DESCRIPTION OF THE INVENTION

This invention relates to a biologically derived, biocompatible, non-antigenic, and incorporatable material for use as a generic bone substitute, as well as the process for making this material. The bone substitute material is derived from glutaraldehyde-tanned bone, which has been found to be highly biocompatible. Host bone readily invades glutaraldehyde-tanned bone when the latter material is implanted adjacent to the host bone.

Treatment with glutaraldehyde stabilizes the material and also renders it non-antigenic by cross-linking proteins. Due to the non-antigenicity, the bone stock from which the material is derived can be obtained from autogenous or exogenous sources. Widely available and suitable bone sources include, but are not limited to, bovine, ovine, equine, and porcine.

The bone grafting material derived from the bone stock may be in several forms, depending on the specific bone defect that the grafting material will be used to repair. The forms include, but are not limited to, the following: (a) a block that is later shaped by the surgeon to the actual contour of the defect; (b) in pulverized form (particle size ranging from less than 100 u to exceeding 300 u) suspended in a gelatinous carrier (biological or non biological in nature) that is applied to the defect and later solidifies; (c) a semisolidified, moldable carrier that is impregnated with pulverized bone; and (d) predetermined shapes (e.g. cylinders) that will be used for large defect filling. In the forms identified in (b) and (c) above, the particle size employed is dependent upon the degree of bone density desired (i.e. a smaller particle size will yield a higher density of new bone which may have an application in load bearing situations).

Conventional machining techniques may be used to shape the bone into a precise predetermined form and size. The ability to precisely machine the bone into the exact shape required for repairing a specific defect is one of the advantages of the method of the invention. The resulting bone substitute will retain its form, and a surgeon does not have to shape the material during implantation.

Known methods of comminuting bone, including but not limited to milling, grinding, and pulverizing, can be used to produce pulverized bone with the desired particle size, including a fine powder. Physiological saline may be added to the pulverized/powdered bone in a quantity sufficient to form a paste-like suspension. Alternatively, the bone material is combined with carriers as mentioned above. Such carriers include, but are not limited to, gelatins and polysaccharides. The resulting suspensions may be molded or cast into the desired shape, injected (using a hypodermic syringe) into a bone defect, or shaped to fit a defect during implantation. The carrier may solidify or be resorbed after implantation or may retain its original consistency. Such suspensions may be used to fill various bone defects comprising cavities or tunnels, bone chips, or any small bone defect.

For some purposes, pulverized or powdered bone would not be the preferred grafting material. One example is implantation of bone grafting material at a weight-bearing position.

The grafting material of the invention is suitable for use in repairing a wide range of bone defects which are the result of injury, disease or birth defects. The material can also be used in cosmetic surgery. The material can be implanted in both weight-bearing and non-weight-bearing situations, and a small sampling of the many potential uses follows.

The bone replacement material of the invention can be used to repair such defects as large non-unions (including those too extensive to be bridged by electrical stimulation alone) such as those resulting from multiple fractures or surgical removal of diseased bone portions. Individuals having one arm or leg longer than the other may have a shaped block of the grafting material incorporated into the apporpriate bone to lengthen it. The bone replacement material of the invention is generally strong enough to be used as part of such large, weight-bearing bones as the tibia or the femur.

Treatment of certain fractures, such as those of the hip, sometimes includes drilling a tunnel and inserting a pin until the fracture heals. When the pin is removed, the empty tunnel is filled in slowly by the patient's natural bone-generating mechanism. Faster healing may be achieved by filling the tunnel with the grafting material of the invention. Other uses include maxillio-facial bone reconstruction and filling of defects from bone chips.

The method of producing the bone grafting material of the present invention is a multi-step process in which the order of the steps may vary. The process begins with selection of a bone source. Any suitable readily-available allogenic or xenogenic bone stock may be used, including bovine, porcine, ovine, and equine, as discussed above. If the final desired form of the bone grafting material is a block of bone or a machined shape, the bone stock must be large enough to provide a block of the required size.

The bone stock is obtained fresh, and the desired section of bone is grossly removed by any suitable means such as cutting with a saw, with frequent rinsing in a fluid such as distilled water or saline to keep the bone moist and cool (at or below physiological temperature to prevent denaturation of bone materials (such as collagen). Associated connective tissue (tendons, ligaments, and fascia) is removed. A smaller bone piece that more closely approximates the desired final prosthesis dimensions may be obtained by coring the bone piece using, for example, a hole saw. The bone piece is again rinsed and cooled with fluid during the sawing and afterward to remove debris.

If the bone is to be pulverized rather than machined into a precise shape, the pulverization may be done by any suitable means at any point in this multistep process.

Any conventional means of machining hard materials, including the use of drills, lathes, saws, and other tools, may be used to obtain the desired final shape from the bone piece. The bone piece may then be cleaned to remove machine oils and debris (if the piece was machined) and also to surface defat the material. Any suitable solvent can be used for this purpose. A preferred procedure involves submersion of the bone in 100% ethanol followed by saline rinses.

Advantageously, the bone piece is next treated to increase the porosity of the matrix and thus to further encourage ingrowth of host bone into the grafting material. This treatment may be accomplished by extracting the bone with an organic solvent, such as chloroform, 100% ethanol, chloroform:methanol (1:1), acetone, or similar solvents, followed by rinsing in physiological saline to remove the organic solvent. Optionally, this porosity-increasing step may include treatment of the bone piece with a protease such as Pronase ®, collagenase or hyaluronidase. In a particularly preferred procedure, the bone pieces are submerged in a buffered Pronase ® solution at 37° C. for 24 hours, followed by rinsing in buffered normal saline and extraction with chloroform:methanol (1:1) by submersion for one hour with constant stirring at 25° C., followed by rinsing in buffered normal saline. This treatment removes non-matrix-bound (non-collagenous) proteins. Desirably, all such proteins are removed. If all such proteins are removed, the porosity of the matrix can be increased by as much as 10%. The treatment also further reduces the antigenicity of the material. The level of porosity can be determined by visual inspection and confirmed by light or electron microscopy.

The bone material may be demineralized if desired. Any known demineralizing agent may be used, including but not limited to solutions comprising organic or mineral acids (such as formic acid, hydrochloric acid, nitric acid, citric acid, or oxalic acid) and/or $Ca^{++}$ chelators such as ethylenediaminetetracetate (EDTA). Preferably, the demineralization solution comprises 0.1 to 1.0N HCl, most preferably 0.3N HCl. Advantageously, the solution also comprises up to 1% EDTA, most preferably 0.1% EDTA. The demineralization may serve to increase the porosity of the grafting material. The demineralized bone will have a softer, "spongier" texture than non-demineralized bone, and thus may be useful only in non-weight-bearing situations such as repair of small defects, filling of tunnels or other hollow areas, cosmetic surgery, and similar uses. Pulverized bone processed according to the method of this invention is particularly suitable for demineralization. When the demineralized bone is implanted adjacent to host bone, the host bone may invade it (an osteoinvasion process).

The bone piece is treated with glutaraldehyde under tanning conditions. This tanning step may be done at any point during the multi-step process of deriving the grafting material. The bone stock may be tanned before or after machining or pulverizing, and before or after the porosity-increasing step, for example. Most preferably, the tanning step follows the machining/pulverizing, surface cleaning and defatting, and porosity-increasing steps.

The bone is treated with a solution comprising glutaraldehyde in a concentration sufficient to crosslink available proteins. The glutaraldehyde concentration advantageously is between about 0.2% and about 0.8%, and most preferably about 0.6% (w/v). The solution is preferably buffered with any commonly used buffering agent. Most preferably, the solution is buffered with HEPES. The bone piece is tanned under physiological pH conditions. Advantageously, the pH is between 6.8 and 7.5.

The tanning process is continued until proteins have been cross-linked to a degree sufficient to render the bone non-antigenic when implanted in a host of a species other than the species from which it was derived. The degree of cross-linking must also be sufficient to stabilize the bone material. The stability should be such that the bone-grafting material does not decompose subsequent to implantation, but rather remains intact at least for a time sufficient to allow ingrowth of host bone into the matrix provided by the grafting material. Preferably, the grafting material is stabilized and permanently incorporated into the host bone. The bone is contacted with glutaraldehyde for any length of time that is sufficient to cross-link the proteins to the desired degree. Advantageously, the bone is treated with glutaraldehyde for about one month or more.

The glutaraldehyde treatment imparts many desirable properties to the material. For example, cross-linking of proteins by glutaraldehyde renders the material non-antigenic so that it may be implanted in a host other than the one from which the stock bone was taken to produce the grafting material. Glutaraldehyde-treated bone has been found to have excellent biocompatibility. When glutaraldehyde-treated bone is implanted in mammalian host bone, there is generally no fibrous encapsulation, interposition of fibrous tissue between host bone and implanted bone, or other evidence of rejection. Instead, in the case of non-demineralized bone, host bone grew into the implanted bone, thus incorporating it. By contrast, interposition of fibrous tissue and encapsulation are known problems when implants made of less biocompatible materials are introduced into mammals.

Resorption of implanted bone material is another known problem. The resorbed material may or may not be replaced by the host. In some cases, it may be desirable to implant a prosthesis that is resorbed as host bone replaces it. In such a case, the glutaraldehyde tanning step could be replaced by tanning with a different agent (e.g., formaldehyde or alcohol) which renders the bone material resorbable. In most cases, however, it is desirable that the implanted material retain its shape and position and not be resorbed. The cross-linking that occurs during glutaraldehyde tanning produces a stabilized grafting material that is generally not resorbed.

Following glutaraldehye tanning, the bone piece may be further sterilized by any suitable means, including radiation or immersion in ethanol or bacteriocidal solution. Preferably, a buffered surfactant/formaldehyde ethanol sterilant is used. The grafting material may be stored in a suitable sterile solution such as 0.05% (w/v) glutaraldehyde in HEPES buffer, in sterile containers until needed.

Conventional surgical techniques are used to position the bone grafting material. Generally, the damaged sections of the host bone will be removed and grafting material shaped to replace the missing bone portion will be attached to the host bone. Standard means of attachment, such as wires and screws, intramedullary rods, casts, or external fixation devices may be used to position the grafting material during healing. Growth of the host bone into the graft serves to anchor it, and the wires and screws can be removed at that point if desired.

Alternatively, in cases such as filling of a tunnel left by removal of a surgical pin, machined grafting material may be inserted into the host bone and held by a friction fit. A suspension comprising pulverized bone grafting material suspended in a carrier may also be used to fill such tunnels or small bone defects.

The method of producing the bone grafting material of the present invention is illustrated by the following examples. One skilled in the art will recognize the variations in order of steps, prosthesis shape, and other aspects of the method of the invention and the prostheses so produced, which are within the scope of the invention. Thus, the examples are meant to illustrate, but not limit, the scope of the invention.

EXAMPLE I

Machined Bone Implants

The following procedure was used to derive machined bone implants comprising the bone grafting material of the invention.

Bone plates were cut from fresh deskinned and dehooved bovine hind legs provided by an abattoir. The bone plate was cut anterior to the ankle-tibia joint, in the region of the epiphyseal plate extending anteriorly approximately 1½ to 2". Generally some soft marrow region is included. The associated connective tissue (tendons, ligaments and fascia) were removed prior to transfer to a machine shop, where the bone plates were frozen at 0° C. until processed.

A bone plate was selected that would yield at least a ¾" bone piece devoid of the epiphyseal plate. Bone pieces were taken from both the region anterior to the epiphyseal plate (i.e., the region from the epiphyseal plate to the bone marrow of the long shaft) and posterior to the epiphyseal plate (i.e., the region from the epiphyseal plate to the articular cartilage.)

The bone plate was installed in a drill press vise and cored using a trephine used for clinical biopsy of bone. Distilled water was used to cool and flush the bone as it was being cored. The resulting bone pieces were cylindrical in shape, approximately 0.110 inch in diameter, with a length of approximately ½ inch. The remnant boneplate was discarded.

The bone pieces ("bone cores") were then surface cleaned in 100% ethanol to remove machine oils and debris. The cores were submerged in the alcohol for ½ hour and after the first half hour the alcohol was replaced with fresh 100% ethanol for an additional ½ hour. The alcohol was kept at room temperature, approximately 25° C. The second alcohol rinse was poured off and the bone cores were rinsed in 0.9% normal saline. Initially a quick rinse was used to clean the exterior of the cores and container. This was followed by two 30-minute rinses in 0.9% saline.

The cores were visually inspected for matrix integrity, porosity, and the desired dimensions. Acceptable cores were then tanned by submersion in 0.625% (w/v) glutaraldehyde in HEPES buffer for a minimum of one month.

The bone cores were sterilized by submersion in a 4% formaldehyde/22.5% ethanol/1.2% Tween solution buffered with HEPES, pH 7.4, for a minimum of eight hours and a maximum of 24 hours at 37° C. The cores were next rinsed (four 10-minute rinses and one 6-hour rinse) and stored until needed in 0.05% (w/v) HEPES-buffered glutaraldehyde. Prior to implantation, the cores were rinsed in normal saline until levels of residual glutaraldehyde (as measured by HPLC) were reduced to non-toxic levels.

The cores prepared above were inserted into complementary holes made in the femurs of rabbits using standard surgical techniques. The quadricep muscle was separated and pulled aside over the condyle of the femur and a hole 0.110 to 0.120 inch in diameter was made in the femur extending through the anterior cortex into the marrow region, but not penetrating the posterior cortex. The area was rinsed with saline to remove all debris. The depth of the hole in the femur matched that of the bone core to be inserted, so that the surface of the inserted core would be flush with the condyle surface. Protrusion of the core, which could cause muscular damage or extensive callus formation during the repair process, was thus avoided.

The inserted bone cores were held in place by a friction fit and by the associated quadricep muscle pressure on top. The area was sutured closed and the implanted cores were left in place for between one and six months before being retrieved from individual rabbits. The retrieved cores were histologically evaluated by a veterinary reference laboratory and a report was made on a monthly basis. General findings associated with all studies have shown that there is no fibrous walling off of the implant, and that there is host bone invasion into endosteal, intramedullary (marrow region), and peristeal surfaces. Thus, overall invasion of all bone surfaces has been demonstrated. A phloxine tartrazine stain was used to differentiate new and old bone, as well as delineating whether or not the new bone deposited has been there for a period of time. Newly deposited bone usually exhibits a woven-type bone structure, whereas a lameller-type bone structure is exhibited by older bone. Invasion of the implant by host bone (osteoconduction) was seen in as little as three months.

Cores derived from bone taken from the region posterior to the epiphyseal plate (see above) were found to have slightly more invasion of host bone.

EXAMPLE II

Bone Grafting Material Comprising Pulverized Bone

Bone plates are cut from bovine hind legs as described in Example I. A bone plate is fragmented, and washed with distilled water to remove any water-soluble subtances. The bone is then dried and further pulverized in a liquid nitrogen mill. The material is then sieved and particles in the desired size range (approximately 75 microns) are isolated. The pulverized bone is then submerged in a solution comprising 0.3N HCl and 0.1% EDTA until the bone is completely demineralized. Several washes in distilled water follow, and the bone material is next submerged in 3 washes of 100% ethanol, then dried. The material is extracted with chloroform:methanol (1:1), treated with Pronase ®, and tanned with glutaraldehyde by the procedures described in Example I.

The bone grafting material is rinsed with saline to remove glutaraldehyde (as in Example I) and combined with gelatin and implanted in a tunnel left in host bone upon removal of a surgical pin. The gelatin solidifies after implantation.

We claim:

1. A method of preparing a biocompatible, stable, and non-antigenic bone grafting material from allogenic or xenogenic bone stock comprising
    (a) machining a bone segment to the desired dimensions
    (b) tanning the bone segment by treating it with glutaraldehyde under tanning conditions.
2. The method of claim 1 wherein the bone segment is treated with a tanning solution containing glutaraldehyde in a concentration sufficient to substantially cross-link the proteins in the bone segment.
3. The method of claim 2 wherein the bone segment is treated with a tanning solution comprising about 0.2% to about 0.8% (w/v) glutaraldehyde.
4. The method of claim 3 wherein said tanning solution comprises about 0.6% (w/v) glutaraldehyde.
5. The method of claim 2 wherein said tanning solution further comprises a buffer.
6. The method of claim 5 wherein said buffer comprises HEPES.
7. The method of claim 1 wherein said tanning conditions include a physiological pH.
8. The method of claim 7 wherein said pH ranges from about 6.8 to about 7.4.
9. The method of claim 1 wherein the bone segment is treated with glutaraldehyde for a length of time sufficient to substantially cross-link the proteins in the bone segment.
10. The method of claim 9 wherein the bone segment is treated with glutaraldehyde for a minimum of about one month.
11. The methods of claim 1, 2, 5, 7 or 9 wherein the degree of cross-linking is sufficient to render the bone biocompatible, stable and non-antigenic.
12. The method of claim 1 additionally comprising treating the bone segment with a protease to increase matrix porosity.
13. The method of claim 1 or 12 additionally comprising extracting the bone segment with an organic solvent to increase matrix porosity.
14. The method of claim 1 additionally comprising sterilizing the bone grafting material.
15. The method of claim 1 additionally comprising surface defatting and removing machining oils from the bone segment with ethanol.
16. The method of claim 1 additionally comprising demineralizing the bone segment.
17. A method of preparing a biocompatible and non-antigenic bone grafting material from allogenic or xenogenic bone stock, comprising:
    (a) pulverizing a bone segment to obtain pulverized bone;
    (b) tanning the pulverized bone with glutaraldehyde under tanning conditions;
    (c) combining the pulverized bone with a gelatinous or semi-solidified carrier.
18. The method of claim 17, additionally comprising treating the bone with a protease to increase matrix porosity.
19. The method of claim 17 or 18, additionally comprising extracting the bone with an organic solvent to increase matrix porosity.
20. The method of claim 17 additionally comprising sterilizing the bone grafting material.
21. The method of claim 17 additionally comprising removing fats and machining oils from the bone with ethanol.
22. The method of claim 17 additionally comprising demineralizing the bone.
23. A biocompatible, non-antigenic and stable bone-grafting material comprising allogenic or xenogenic bone stock machined to a desired shape and tanned with glutaraldehyde under tanning conditions.
24. A biocompatible, non-antigenic, and stable bone-grafting material comprising allogenic or xenogenic bone stock that has been pulverized or powdered and tanned with glutaraldehyde under tanning conditions.
25. The bone grafting material of claims 23 or 24 which exhibits osteoconduction when implanted adjacent to host bone.
26. A method of repairing bone defects comprising
    (a) removing damaged or diseased host bone portions that may be present; and
    (b) implanting the bone grafting material of claims 23 or 24 to repair the defect.
27. The method of claim 1 wherein the bone segment is contacted with a buffered tanning solution comprising about 0.2% to about 0.8% (w/v) glutaraldehyde for a minimum of about one month.

* * * * *